United States Patent
Inoue et al.

(10) Patent No.: US 9,164,082 B2
(45) Date of Patent: Oct. 20, 2015

(54) BIOCHIP SUBSTRATE AND METHOD FOR PRODUCING SAME

(75) Inventors: Hidetoshi Inoue, Osaka (JP); Zenya Ashitaka, Osaka (JP); Hiroyuki Kusai, Osaka (JP); Yasushi Takebayashi, Shizuoka (JP); Ryo Morishita, Shizuoka (JP); Yasuo Oka, Fuji (JP)

(73) Assignees: TOYO ALUMINIUM KABUSHIKI KAISHA, Osaka (JP); NIPPON LIGHT METAL COMPANY, LTD., Tokyo (JP)

( * ) Notice: Subject to any disclaimer, the term of this patent is extended or adjusted under 35 U.S.C. 154(b) by 0 days.

(21) Appl. No.: 14/240,281
(22) PCT Filed: Aug. 22, 2012
(86) PCT No.: PCT/JP2012/071218
§ 371 (c)(1),
(2), (4) Date: Feb. 21, 2014
(87) PCT Pub. No.: WO2013/027777
PCT Pub. Date: Feb. 28, 2013

(65) Prior Publication Data
US 2014/0220316 A1    Aug. 7, 2014

(30) Foreign Application Priority Data
Aug. 23, 2011  (JP) ................. 2011-181450

(51) Int. Cl.
*B32B 3/00* (2006.01)
*G01N 33/50* (2006.01)
(Continued)

(52) U.S. Cl.
CPC .............. *G01N 33/50* (2013.01); *G01N 21/01* (2013.01); *G01N 21/65* (2013.01);
(Continued)

(58) Field of Classification Search
CPC .................................. C23C 8/60; C23C 22/00
See application file for complete search history.

(56) References Cited

U.S. PATENT DOCUMENTS

| 7,327,556 B2 * | 2/2008 | Ro et al. ......................... 361/502 |
| 7,616,430 B2 * | 11/2009 | Ro et al. ......................... 361/529 |

(Continued)

FOREIGN PATENT DOCUMENTS

| EP | 1 609 878 A1 | 12/2005 |
| EP | 2 306 197 A1 | 4/2011 |

(Continued)

OTHER PUBLICATIONS

International Search Report issued in PCT/JP2012/071218, dated Oct. 23, 2012.

(Continued)

*Primary Examiner* — Elizabeth Mulvaney
(74) *Attorney, Agent, or Firm* — Birch, Stewart, Kolasch & Birch, LLP

(57) ABSTRACT

A substrate for biochips, which does not induce autofluorescence, which can immobilize a biologically relevant substance(s) easily, which can prevent the undesirable spread of a liquid spot which is added dropwise on the biochips when using the biochips, in which the adhesion between a carbon-containing layer and an aluminum material is high, and which can be produced at lower cost than the known substrate for biochips; a method for producing the substrate; and a biochip including the substrate are disclosed. The substrate for biochips comprises a carbon-coated aluminum material, wherein the carbon-coated aluminum material comprises an aluminum material and a carbon-containing layer formed on at least one surface of the aluminum material, and further comprises an interposing layer which is formed between the aluminum material and the carbon-containing layer, and which interposing layer contains aluminum element and carbon element.

13 Claims, 4 Drawing Sheets

(51) Int. Cl.
*G01N 21/01* (2006.01)
*G01N 21/65* (2006.01)
*G01N 33/553* (2006.01)
*G01N 33/543* (2006.01)
*C23C 22/00* (2006.01)
*C23C 8/60* (2006.01)

(52) U.S. Cl.
CPC ....... *G01N 33/54306* (2013.01); *G01N 33/553* (2013.01); *C23C 8/60* (2013.01); *C23C 22/00* (2013.01); *Y10T 428/24851* (2015.01); *Y10T 428/31678* (2015.04)

(56) References Cited

U.S. PATENT DOCUMENTS 7,639,475 B2 * 12/2009 Ro et al. .................. 361/516
2006/0171102 A1 8/2006 Ro et al.
2006/0228813 A1 10/2006 Wu et al.
2011/0027537 A1 * 2/2011 Inoue et al. .................. 428/172
2011/0152409 A1 6/2011 Nokihara et al.

FOREIGN PATENT DOCUMENTS

JP 2010-8378 A 1/2010
WO WO 2004/087984 A1 10/2004
WO WO 2010/086961 A1 8/2010

OTHER PUBLICATIONS

European Office Action dated Mar. 26, 2015 for EP Application No. 12826026.2.

* cited by examiner

BIOCHIP SUBSTRATE AND METHOD FOR PRODUCING SAME

TECHNICAL FIELD

The present invention relates to a substrate for biochips such as a protein chip, peptide chip and DNA chip, a method for producing the same and a biochip comprising the same.

BACKGROUND ART

Biochips such as a protein chip, peptide chip and DNA chip are widely used for diagnosis and research of various diseases. The biochips which have been widely used are usually obtained by immobilizing biologically relevant substances such as a protein, peptide and DNA on a glass substrate such as a slide glass.

However, the conventional biochips using the glass substrate were likely to cause non-specific adsorption and had a problem in accuracy of measurement. Also, since the glass substrate induces autofluorescence, measurements employing fluorescent labels which have been often used recently, had a problem in accuracy.

In order to solve these problems, a substrate for biochips, in which a carbon-containing layer having an active group(s) is formed on a metal substrate, and a biologically relevant substance(s) is/are bound to the active group(s), is provided (Patent Document 1). This substrate for biochips has excellent properties that autofluorescence is not induced, a biologically relevant substance(s) can be immobilized easily, processing of the substrate is easy, and high flatness and surface precision can be attained. However, to increase the adhesion between the metal substrate and the carbon-containing layer in this substrate for biochips, it is necessary to form a nickel-phosphorus (NiP) layer therebetween by an electroless plating, which results in high cost.

Further, a substrate for biochips, in which an amino group-containing polymer is covalently bound on the substrate at least the surface of which is composed of carbon, is also provided (Patent Document 2). The biologically relevant substance is covalently bound to the amino group. This substrate for biochips also has excellent properties as that described in Patent Document 1. However, in cases where the whole substrate is formed as carbon substrate such as amorphous carbon, calcination for about one month is necessary for carbonization of a resin, which requires production cost and time. In cases where a carbon-containing layer is formed on the metal substrate, as in the substrate for biochips described in Patent Document 1, it is necessary to form a nickel-phosphorus (NiP) layer between the metal substrate and the carbon-containing layer by an electroless plating for increasing the adhesion therebetween, thereby resulting in high cost.

On the other hand, a carbon-coated aluminum material, in which a carbon-containing layer is formed on the surface of an aluminum material, and further an interposing layer composed of aluminium carbide is formed therebetween, is known (Patent Document 3). This carbon-coated aluminum material is suitably used as an electrode structure such as an electrochemical capacitor and electrolytic condenser, and use as a substrate for biochips is not described or suggested in Patent Document 3.

PRIOR ART DOCUMENTS

Patent Document

Patent Document 1: JP 2006-329686 A
Patent Document 2: JP 2010-008378 A
Patent Document 3: JP 4445465 B

SUMMARY OF THE INVENTION

Problems to be Solved by the Invention

An object of the present invention is to provide a substrate for biochips, which does not induce autofluorescence, which can immobilize a biologically relevant substance(s) easily, which can prevent the undesirable spread of a liquid spot which is added dropwise on the biochip when using the biochips, in which the adhesion between a carbon-containing layer and an aluminum material is high, and which can be produced at lower cost than the known substrate for biochips described in Patent Document 1 or Patent Document 2; a method for producing the substrate; and a biochip including the substrate.

Means for Solving the Problems

The present inventors intensively studied to find out that by using a substrate for biochips, the substrate comprising a specific carbon-coated aluminum material, autofluorescence is not induced, a biologically relevant substance(s) can be immobilized easily, the undesirable spread of a liquid spot added dropwise on the biochips when used can be prevented, the necessity of a NiP electroless plating for increasing the adhesion between a carbon-containing layer and an aluminum material is eliminated, and the substrate can be produced at low cost, thereby completing the present invention.

That is, the present invention provides a substrate for biochips, the substrate comprising a carbon-coated aluminum material, wherein the carbon-coated aluminum material comprises an aluminum material and a carbon-containing layer formed on at least one surface of the aluminum material, and further comprises an interposing layer which is formed between the aluminum material and the carbon-containing layer, which interposing layer contains aluminum element and carbon element. Also, the present invention provides a biochip in which one or more biologically relevant substances are bound on the substrate for biochips according to the above-described present invention. Also, the present invention provides a method for producing a substrate for biochips, the substrate comprising a carbon-coated aluminum material, wherein the method comprises the steps of: a first step of providing an aluminum material; a second step of placing the aluminum material in a space containing a hydrocarbon-containing substance; and a third step of heating said aluminum material while being placed in the space containing the hydrocarbon-containing substance. Further, the present invention provides a method for producing a biochip, the method comprising a step of producing a substrate for biochips by the above-described method of the present invention; and a step of binding one or more biologically relevant substances on the obtained substrate for biochips.

Effect of the Invention

The substrate for biochips of the present invention does not induce autofluorescence, which can immobilize a biologically relevant substance(s) easily, which can prevent the undesirable spread of a liquid spot added dropwise on the biochips when used, the necessity of a NiP electroless plating for increasing the adhesion between a carbon-containing layer and an aluminum material is eliminated, and which can be produced by a simple method of heating the aluminum material in an atmosphere containing a hydrocarbon, thereby allowing the production of the substrate at low cost.

BEST MODE FOR CARRYING OUT THE INVENTION

Figure 1:
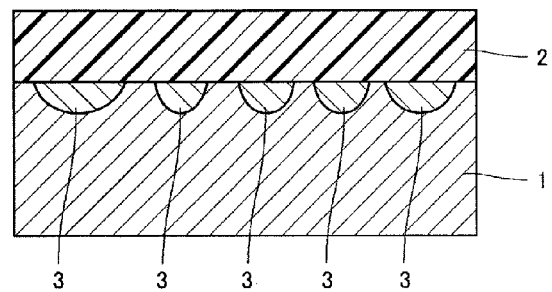
FIG. 1 is a schematic cross-sectional view showing the carbon-coated aluminum material constituting the substrate for biochips of Example 1 of the present invention.

The substrate for biochips of the present invention comprises a carbon-coated aluminum material, wherein the carbon-coated aluminum material comprises an aluminum material and a carbon-containing layer formed on at least one surface of the aluminum material, and further comprises an interposing layer which is formed between the aluminum material and the carbon-containing layer, which interposing layer contains aluminum element and carbon element.

Each constituent of the substrate for biochips of the present invention will now be described in detail.

The substrate for biochips of the present invention is not restricted as long as the substrate comprises a specific carbon-coated aluminum material, and the substrate may be composed of the carbon-coated aluminum material alone, or may be composed of a substrate body and the carbon-coated aluminum material laminated on the substrate body.

In cases where the substrate for biochips of the present invention is composed of the substrate body and the carbon-coated aluminum material, the substrate body to be used is not restricted as long as the substrate does not induce autofluorescence and is hard and flat, which characteristics are suitable for forming the substrate for biochips. As the substrate body, a glass plate, plastic plate and metal plate such as aluminum, titanium or stainless steel may be preferably used. If the substrate body is warped or the surface thereof is irregular, the diffuse reflection is large or the focusing in detection is difficult, so that the S/N ratio in detection is decreased. Therefore, it is preferable that the substrate body is flat and the surface thereof is smooth. For this reason, in cases where the metal plate is used as the substrate body, it is preferable that the substrate body was annealed under pressure after sizing such as punching to eliminate the strain and promote the flatness, and after grinding the surface to make it smooth, the surface was further polished to increase the surface precision to produce the substrate body. These workings for attaining flatness and smoothness can be carried out by conventional metal working methods.

In cases where the substrate for biochips of the present invention is composed of the substrate body and the carbon-coated aluminum material, the carbon-coated aluminum material is laminated on the substrate body. The carbon-coated aluminum material comprises a carbon-containing layer formed on at least one surface of the aluminum material, and comprises an interposing layer which is formed between the aluminum and the carbon-containing layer, which interposing layer contains aluminum element and carbon element. Each of the constituting elements will now be described dividedly.

Aluminum Material

The aluminum material used as a base material on which the carbon-containing layer is formed, is not particularly restricted, and pure aluminum or an aluminum alloy may be used. The purity of aluminum in the aluminum material is preferably not less than 98% by mass in terms of the value measured according to the method described in "JIS H2111". The aluminum material used in the present invention contains an aluminum alloy to which at least one alloy element selected from the group consisting of lead (Pb), silicon (Si), iron (Fe), copper (Cu), manganese (Mn), magnesium (Mg), chromium (Cr), zinc (Zn), titanium (Ti), vanadium (V), gallium (Ga), nickel (Ni) and boron (B) were added as components within the necessary range, or also contains aluminum having the above-described inevitable impurity elements in a restricted amount. The thickness of the aluminum material is not particularly restricted, and the thickness thereof is preferably not less than 5 μm and not more than 200 μm for a foil, and preferably higher than 200 μm and not more than 3 mm for a plate. More preferably, the thickness of the aluminum material is preferably set such that the whole thickness of the substrate for biochips, including the substrate body, is within the range not more than 1.5 mm.

As the above-described aluminum material, the material produced by a known method may be used. For example, a molten metal of aluminum or the aluminum alloy having the prescribed composition is prepared, and an ingot obtained by casting the molten metal is properly subjected to a homogenization treatment. Then, the treated ingot is subjected to a hot rolling and cold rolling to obtain the aluminum material. An intermediate annealing treatment may be carried out at a temperature of not less than 150° C. and not more than 400° C. during the cold rolling step.

Carbon-Containing Layer

The carbon-containing layer is a layer used for the binding with a biologically relevant substance(s) such as a protein, peptide and/or DNA via an active group(s) which is(are) given to the carbon-containing layer.

The carbon-containing layer is not particularly restricted as long as the layer is composed of one containing at least carbon element. For example, the carbon-containing layer can be formed on the surface of the aluminum material by heating the aluminum material under the conditions described below in a space containing a hydrocarbon-containing substance. Also, the carbon-containing layer can be formed on the surface of the aluminum material by attaching carbon-containing substances such as activated carbon fibers, activated charcoal clothes, activated carbon felts, activated carbon powders, India inks, carbon blacks, graphites and various resins on the surface of the aluminum material, and then by heating the resultant in a space containing a hydrocarbon-containing substance under the conditions described below.

The carbon-containing layer is preferably an organic layer containing a carbon precursor, which organic layer is obtained by heating various resins in a space containing a hydrocarbon-containing substance.

The carbon-containing layer is preferably the organic layer containing a carbon precursor, because the surface thereof is compact and the spread of a liquid spot can be prevented upon adding the liquid dropwise thereto when using the biochips.

When the organic layer is formed, resins having the property that volatilization does not occur during heating in an atmosphere containing a hydrocarbon at a temperature of not less than 450° C. and less than 660° C. for not less than 1 hour and not more than 100 hours, are preferably used. This is because defects or cracks are generated on the organic layer due to the volatilization of the organic layer during the step of forming the layer. Preferable examples of the resins for forming the organic layer include polyvinyl alcohol resins, polyvinyl butyral resins, epoxy resins, resins having a cyclic structure such as an aromatic (for example, phenol resins) and acrylic resins. In particular, phenol resins are preferably used from the viewpoint of the prevention of the spot spread. The carbon precursor preferably has a peak(s) of Raman scattering intensity at a Raman Shift of about 1350 $cm^{-1}$ and/or about 1580 $cm^{-1}$ in Raman spectrum detected by Raman spectroscopy. Since the peak of Raman scattering intensity at about 1350 $cm^{-1}$ is the peak of amorphous carbon, and the peak of Raman scattering intensity at about 1580 $cm^{-1}$ is the peak of graphite, the carbon precursor having these peak(s) means that the carbon precursor having at least partially amorphous carbon structure and/or graphite structure.

The carbon-containing layer constituting the substrate for biochips of the present invention has a flat surface and easily gives sufficient amount of the active group(s) used for the binding with a biologically relevant substance(s). As is concretely shown in Examples below, in the substrate for biochips of the present invention, the spread of a spot is prevented when adding various solvents dropwise thereto, and in particular, the spread of a spot is prevented to almost the same extent as that of the substrate the entire of which is composed of amorphous carbon. Further, in cases where the carbon-containing layer constituting the substrate for biochips of the present invention is composed of the organic layer containing a carbon precursor, a sufficient amount of the active group(s) used for the binding with a biologically relevant substance(s) can be given easily, and in particular, the spread of a spot is more prevented compared to the substrate the entire of which is composed of amorphous carbon. In cases where the carbon-containing layer is the organic layer containing a carbon precursor, activated carbon fibers, activated charcoal clothes, activated carbon felts, activated carbon powders, India inks, carbon blacks, graphites and the like may be contained as necessary.

The carbon-containing layer may be formed on one side of the aluminum material and may be formed on both sides thereof. Although only one side of the aluminum material is necessary when used as the biochips, it is simpler to form the carbon-containing layers on both sides thereof during the production process. The thickness of the carbon-containing layer is not particularly restricted as long as the function as the biochips is exerted, and thickness thereof is about 0.1 μm to about 5 mm, preferably about 0.5 μm to about 1 mm.

The carbon-containing layer may be composed of a single layer, and may be composed of a plurality of layers. In particular, in cases where the carbon-containing layer formed on the surface of the aluminum material is composed of a plurality of layers, it is preferable that the layers other than the outermost layer among the plurality of carbon-containing layers formed on the surface of the aluminum material, more preferably the layer formed as a first carbon-containing layer is composed of an organic layer containing a carbon precursor, and a second carbon-containing layer is formed on the surface of the first carbon-containing layer. By having the carbon-containing layer having such a structure, when the substrate for biochips of the present invention is used for biochips and physiological buffered saline is used as below mentioned, the corrosion of the aluminum material can be suppressed.

For the reason why the corrosion of the aluminum material can be suppressed by having the carbon-containing layer having such a structure, it is presumed that the carbon-containing layers formed on the surface of the aluminum material, which layers are other than the outermost layer and are composed of organic layers containing carbon precursors (more preferably the first layer), are compact, and therefore, the carbon-containing layers function as barrier layers of the surface of the aluminum material, and penetration of physiological buffered saline into the surface of the aluminum material is prevented, thereby suppressing the corrosion of the aluminum material.

The outermost layer among the plurality of carbon-containing layers formed on the surface of the aluminum material is not particularly restricted as long as the layer is a carbon-containing layer composed of one containing at least the above-described carbon element.

Interposing Layer

Figure 2:
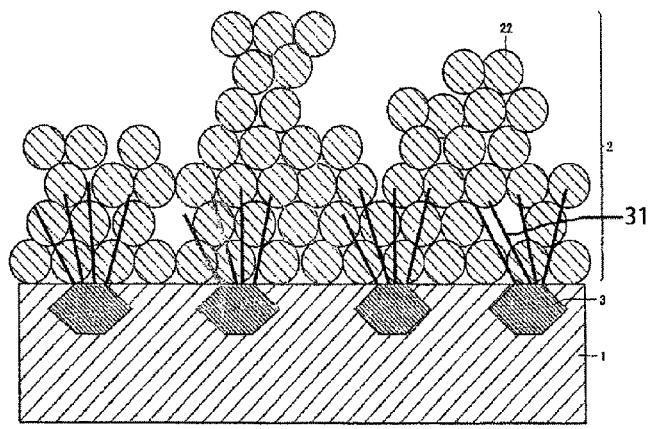
FIG. 2 is a schematic cross-sectional view showing the carbon-coated aluminum material constituting the substrate for biochips of Example 2 of the present invention.

The interposing layer is formed between the aluminum material and the carbon-containing layer, and contains aluminum element and carbon element. An example of the interposing layer is schematically shown in FIG. 1 and FIG. 2. FIG. 1 and FIG. 2 are schematic cross-sectional views of the carbon-coated aluminum materials constituting the substrate for biochips, FIG. 1 is a schematic cross-sectional view of the carbon-coated aluminum material prepared in Example 1, and FIG. 2 is a schematic cross-sectional view of the carbon-coated aluminum material prepared in Example 2. In FIG. 1 and FIG. 2, 1 is the aluminum material, and the carbon-containing layers 2 are formed on both sides of the aluminum material respectively. In FIG. 1 and FIG. 2, the interposing layer 3 is partially formed on each surface of the aluminum material. In FIG. 1 and FIG. 2, the interposing layer 3 is formed in the form of islands from a planar viewpoint on the surface of the aluminum material. FIG. 1 and FIG. 2 are nothing more than examples, and therefore the interposing layer 3 is not restricted to FIG. 1 and FIG. 2, and may be formed on the entire surface of the aluminum material. In FIG. 2, although the fiber-like structure 31 extends from the surface of each interposing layer 3 into the carbon-containing layer, FIG. 2 is nothing more than an example, the fiber-like structure 31 is not restricted to FIG. 2 and may have any form as long as the structure 31 extends from the surface of each interposing layer 3 into the carbon-containing layer (e.g. filamentary structure, cactus structure and the like). Although each interposing layer 3 in FIG. 2 has fiber-like structure 31, the fiber-like structure 31 is not necessary as long as the interposing layer 3 exists. As described above, the interposing layer 3 contains aluminum element and carbon element, and preferably contains aluminium carbide.

Owing to the presence of the interposing layer, the adhesion between the aluminum material and the carbon-containing layer is increased, and detachments and cracks of the carbon-containing layer do not occur. Therefore, the necessity to form a nickel-phosphorus electroless plating layer between the substrate body and the carbon-containing layer as in known substrates for biochips described in Patent Document 1 and Patent Document 2, is eliminated, and the substrate can be produced at low cost.

Next, the method for producing a substrate for biochips of the present invention will now be described.

First Step

Firstly, the above-described aluminum material is provided.

In the production method of the present invention, in cases where the thin carbon-containing layer is formed, the adhesion between the aluminum material and the carbon-containing layer can be increased only by placing the aluminum material in a space containing a hydrocarbon-containing substance and heating the aluminum material as in the below-mentioned second step and third step, and only by making the above-described interposing layer exist.

However, in cases where the thick carbon-containing layer is formed, the step of attaching a carbon-containing substance on the surface of the aluminum material is preferably included in order to ensure the adhesion between the aluminum material and the carbon-containing layer.

The carbon-containing substance is not particularly restricted. For example, the carbon-containing layer can be formed on the surface of the aluminum material by attaching carbon-containing substances such as activated carbon fibers, activated charcoal clothes, activated carbon felts, activated carbon powders, India inks, carbon blacks, graphites and various resins on the surface of the aluminum material, and then heating the resultant in a space consisting a hydrocarbon-containing substance under the conditions described below.

These carbon-containing substances can be applied on the surface of the aluminum material by using a mixture in which the substances are dispersed with a binder in a solvent. The binder used herein is preferably an organic macromolecule which is combustible when heated, and as preferable examples thereof, synthetic resins such as polyvinyl chloride, carboxyl-modified polyolefin resins, vinyl acetate resins, vinyl chloride resins, vinyl chloride-vinyl acetate copolymer resins, vinyl alcohol resins, polyvinyl fluoride resins, acrylic resins, polyester resins, urethane resins, epoxy resins, urea resins, phenol resins, acrylonitrile resins, nitrocellulose resins, paraffin wax and polyethylene wax; was or tar, and native resins such as glue, sumac, pine resin and beeswax, or wax may be suitably used. Depending on the molecular weight and kind of the resins, some of these binders volatilize when heated, and some of them remain as the carbon precursors in the carbon-containing layer by thermal decomposition. The binder may be diluted with an organic solvent or the like to adjust the viscosity. As the organic solvent, a conventional organic solvent such as methyl iso-butyl ketone, toluene or methyl ethyl ketone may be used. The thickness of the carbon-containing substance to be applied can be adjusted properly depending on the intended thickness of the carbon-containing layer, and for example, the thickness is preferably between 0.1 µm and 5 mm, more preferably between 0.5 µm and 1 mm.

In cases where the carbon-containing layer to be foil led is the organic layer containing a carbon precursor, a resin layer composed of various resins such as phenol resins described above may be formed on the surface of the aluminum material. The step of forming the resin layer preferably includes the step of mixing the resin and the solvent (mixing step). By having the mixing step, the resin layer can be formed uniformly on the surface of the aluminum material, and the organic layer to be formed through the subsequent step can be formed uniformly on the surface of the aluminum material. As a result, the organic layer having a compact structure is formed uniformly on the surface of the aluminum material. As the method for forming the resin layer on the surface of the aluminum material in the step of forming the resin layer, a slurry or liquid prepared with the resin and the solvent if needed may be attached by coating, dipping and the like; and a solid prepared may be attached by dispersion in the form of powders, extrusion, heat pressing and the like on the surface of the aluminum material. The solvent used in the step of forming the resin layer is not particularly restricted, and is preferably the solubilizer of the resin (a solvent in which the resin is easily dissolved). In cases where an oil soluble resin is used as the resin, examples of the solvent include methyl iso-butyl ketone, toluene and methyl ethyl ketone. The thickness of the organic layer to be applied may be properly adjusted depending on the intended thickness of the carbon-containing layer and is not particularly restricted, and for example, the thickness thereof is preferably 0.1 µm to 5 mm, and more preferably 0.5 µm to 1 mm. As for drying before heating, the drying temperature and drying time are not particularly restricted as long as the organic solvent is evaporated, and usually the drying may be carried out at a temperature between 20° C. to 300° C. for about 15 seconds to about 1 minute. The mixing method and mixing time are not also restricted as long as the resin layer is formed uniformly. The amount of the solvent is preferably not less than 50% by mass with respect to the amount of the resin to be added.

In cases where the carbon-containing layer to be formed is composed of a plurality of layers, the above-described step of attaching a carbon-containing substance may be carried out a plurality of times in accordance with the desired layers.

In cases where the layers other than the outermost layer among the plurality of carbon-containing layers formed on the surface of the aluminum material, for example, the layer formed as the first carbon-containing layer is desired to be composed of an organic layer containing a carbon precursor, the resin layer composed of the various resins such as phenol reins described above may be formed on the surface of the aluminum material in the step of attaching the carbon-containing substance as in the above-described formation of the organic layer containing the carbon precursor.

When each of the layers is formed, the layer may be dried to evaporate the solvent each time the step of attaching the carbon-containing substance is carried out, or the subsequent step of attaching the carbon-containing substance may be carried out without drying the layer. However, in cases where the subsequent step of attaching the carbon-containing substance is carried out without drying the layer, the solvent may be sharply volatilized to generate bubbles (bubbling) in each layer on heating in the subsequent third step. Therefore, it is preferred to dry the layer to evaporate the solvent each time the step of attaching the carbon-containing substance is carried out. Also in this drying, the drying temperature and drying time are not particularly restricted, and usually the drying may be carried out at a temperature between 20° C. to 300° C. for about 15 seconds to about 1 minute.

Second Step

The aluminum material obtained after carrying out the first step is placed as it is in a space containing a hydrocarbon-containing substance. The hydrocarbon used herein is not particularly restricted, and examples thereof include paraffin hydrocarbons such as methane, ethane, propane, n-butane, isobutane and heptane; olefin hydrocarbons such as ethylene, propylene, butene and butadiene; acetylene hydrocarbons such as acetylene and the like; and derivatives of these hydrocarbons. Among these hydrocarbons, paraffin hydrocarbons such as methane, ethane and propane are preferable due to the gaseous form thereof in the step of heating the aluminum material. More preferable is any one hydrocarbon among methane, ethane and propane, and most preferable hydrocarbon is methane. The hydrocarbon may be used individually, or two or more of these may be used in combination.

The hydrocarbon-containing substance may be any form of liquid, gas or the like. The hydrocarbon-containing substance may be introduced into the space by any method in which space the aluminum material is to be placed as long as the substance is made to exist in the space in which the aluminum material exists. For example, in cases where the hydrocarbon-containing substance is gas (methane, ethane, propane and the like), the hydrocarbon-containing substance may be filled individually or with inert gas into an enclosed space in which the heat treatment of the aluminum material in a third step described below is carried out. In cases where the hydrocarbon-containing substance is liquid, the hydrocarbon-containing substance may be filled individually or with inert gas such that the substance is vaporized in the enclosed space.

Third Step

After the second step, the aluminum material is heated while being placed in the space containing the hydrocarbon-containing substance.

In this step, the pressure of the heating atmosphere is not particularly restricted, and may be normal pressure, reduced pressure or increased pressure. Since the heating under normal pressure is simplest and economical, usually normal pressure is preferably employed. As required, the pressure may be controlled at any point of the term during which a certain heating temperature is maintained; the term during which the space is heated to a certain heating temperature; and the term during which the space is cooled from a certain heating temperature.

In the second step and the third step, the mass ratio of the hydrocarbon introduced into the space in which the aluminum material is heated is not particularly restricted, and usually the mass ratio within the range of not less than 0.1 parts by mass and not more than 50 parts by mass in terms of carbon with respect to 100 parts by mass of aluminum is preferable, and in particular, the mass ratio within the range of not less than 0.5 parts by mass and not more than 30 parts by mass is preferable.

In the third step, the heating temperature may be properly set depending on the composition and the like of the aluminum material to be heated, and usually the heating temperature within the range of not less than 450° C. and less than 660° C. is preferable, and within the range of not less than 530° C. and less than 620° C. is more preferable. However, the heating at a temperature less than 450° C. is not excluded in the production method of the present invention, and the heating may be carried out at a temperature at least higher than 300° C. The heating time is generally within the range of not less than 1 hour and not more than 100 hours depending on the heating temperature and the like.

The surface of the aluminum material may also be roughened before the heat treatment. The roughening method is not particularly restricted, and known techniques such as washing, etching and blasting may be employed.

By using the above-described method, the carbon-coated aluminum material used for the substrate for biochips of the present invention can be obtained. Further, after the third step, the step of cooling the obtained carbon-coated aluminum material and heating the material again, that is, the step of activation treatment may also be carried out. In this case, the step of cooling the carbon-coated aluminum material and heating the material again is preferably carried out at a temperature range of not less than 100° C. and less than 660° C. The obtained carbon-coated aluminum material may also be used as it is as the substrate for biochips.

Next, the case where the substrate for biochips of the present invention is composed of the substrate body and the carbon-coated aluminum material will now be described.

The carbon-coated aluminum material obtained through the first step to the third step is laminated on the substrate body. Although the laminating method is properly selected depending on the material constituting the substrate body and is not particularly restricted, examples thereof include thermal adhesion with a heat sealer, extrusion lamination, and the use of adhesives, gluing agent and the like. However, when the adhesives and gluing agents are used, the adhesive components and the gluing agent components may be melted or swollen by an organic solvent such as DMSO (dimethyl sulfoxide) or the like. Therefore, the thermal adhesion with a heat sealer through a commercially available resin film for heat press is preferable because the thermal adhesion is not adversely affected by the organic solvent such as DMSO and the lamination can be carried out easily.

Although the thus obtained substrate for biochips of the present invention can be used as it is as the substrate for biochips, the exposed portions of aluminum from the carbon-coated aluminum material may remain, so that the obtained substrate is preferably subjected to an anticorrosion treatment of aluminum. Since physiological buffered saline is often used when using the biochips, the remaining portions of the exposed aluminum may cause corrosion, which is not preferred.

In particular, as for the carbon-containing layer having a thickness of not more than 2 µm, for example, in cases where the carbon-containing layer contains carbon particles such as carbon black and the like, physiological buffered saline may be impregnated through the gap between the carbon particles and contacts with the surface of the aluminum material, thereby causing the aluminum material to corrode.

In this case, the corrosion of the aluminum material can be suppressed by employing the structure in which the carbon-containing layer formed on the surface of the aluminum material is composed of a plurality of layers; the layers other than the outermost layer among the plurality of carbon-containing layers formed on the surface of the aluminum material, more preferably the layer formed as the first carbon-containing layer is further composed of organic layers containing carbon precursors; and the second carbon-containing layer is formed on the surface of the first carbon-containing layer.

As the anticorrosion treatment of aluminum, the method of immersing the entire substrate in conversion treatment solution containing anticorrosives which do not chemically react with the carbon substrate in the carbon-containing layer to produce compounds, and which do not generate functional groups on the surface of the carbon substances; or the method of coating the entire substrate with the conversion treatment solution is preferable. Such anticorrosives are preferably ones which form aluminium fluoride, aluminum oxide, zirconium oxide, chromium oxide and silicon oxide, and a mixture thereof; and more specific examples thereof include sodium silicate, chromate solution and chromium-free conversion treatment solution. The solvent of the conversion treatment solution is not restricted as long as the solvent can dissolve the anticorrosives which do not chemically react with the carbon substance in the carbon-containing layer to produce compounds, and which does not generate functional groups on the surface of the carbon substance. Examples thereof include organic solvents including water, alcohols such as ethanol and 2-butanol, acetone, methyl ethyl ketone and toluene. The concentration of the anticorrosives in the conversion treatment solution is not restricted, and usually the concentration is from about 0.1% by mass to about 99% by mass.

The biologically relevant substance(s) is(are) immobilized on the thus obtained substrate for biochips. For this immobilization, it is preferable that the active group(s) is(are) bound to the carbon substances contained in the carbon-containing layer, and the biologically relevant substance(s) such as a protein, peptide and/or DNA is(are) bound through the active group(s).

The active group(s) can be given by forming the carbon-containing layer as described above, and then binding the active group(s) to the carbon-containing layer. The active group(s) is(are) not particularly restricted, and examples thereof include an amino group, aldehyde group, carboxyl group, sulfhydryl group and epoxy group which are covalently bound to carbon. Among these, an amino group is especially preferable because it is versatile and can bind to the biologically relevant substance easily. These functional group(s) to be covalently bound to carbon can be covalently bound to the carbon by cleaving C—C bond, C=C bond and/or C—O bond of the carbon by irradiation of plasma or ultraviolet light, and by binding the resulting carbon radical with the functional group(s) or a compound(s) having the functional group(s). For example, an amino group can be covalently bound to carbon by irradiating the carbon-containing layer with ultraviolet light in the air to convert oxygen in the air to ozone and to react the resulting ozone with the carbon, then after evacuation, by reacting chlorine gas with the resultant to chlorinate the carbon, and, after evacuation, by reacting ammonia gas with the resultant to aminate the carbon. Alternatively, an amino group can also be directly introduced by irradiation of ammonia plasma. Still alternatively, an amino group can be generated on the surface by generating radicals by irradiating the substrate surface with argon plasma, converting the radicals to peroxide by air oxidation, and by reacting the resulting peroxide with allylamine or the like. An aldehyde group can be obtained by, for example, converting the surface of the carbon to an acid chloride, and reducing the resulting acid chloride. A carboxyl group may be obtained by, for example, converting an amino group to a diazonium ion, converting the resulting diazonium ion to nitrile, and hydrolyzing the resulting nitrile. The carboxyl group can also be obtained by oxidizing an alkyl group with potassium permanganate or the like. A Sulfhydryl group can be obtained by, for example, halogenating the surface of the carbon with light or the like, and reacting the generated halogenated alkyl with a thiol. An epoxy group may be generated by treating the carbon-carbon double bond with a peracid. Any of these reactions may be carried out based on the reactions in the field of organic synthetic chemistry, which are well-known by those skilled in the art. The active group(s) is(are) not necessarily bound to carbon by covalent bond, but a compound(s) having the active group(s) may be noncovalently attached by physical adsorption to the carbon-containing layer. For example, an amino group may be given to the carbon-containing layer by physically adsorbing poly-lysine to the carbon-containing layer, which poly-lysine is obtained by polycondensation of lysine which is an amino acid having an amino group in its side chain. The density of the active group(s) given to the carbon-containing layer is not restricted, and is usually about 50 pmol to about 200 pmol, preferably about 100 pmol to about 200 pmol per 1 $cm^2$ of the carbon-containing layer.

The biochip can be obtained by immobilizing one or more biologically relevant substances on the substrate for biochips of the present invention. Here, examples of the biologically relevant substances include nucleic acids such as DNA and RNA; various proteins, antibodies, enzymes and peptides such as synthetic peptides and natural peptides; saccharides such as polysaccharides and oligosaccharides; various lipids; and complexes thereof (glycoproteins, glycolipids, lipoproteins and the like). The cells per se can also be immobilized, and the cell per se is also included within the scope of the term "biologically relevant substance" of the present invention. Further, low molecular weight compounds such as coenzymes, antigen epitopes and haptens are also included within the scope of the term "biologically relevant substance" of the present invention because they specifically interact with biopolymers such as enzymes and antibodies. The biologically relevant substance(s) may be bound to the carbon-containing layer as they are, or the biologically relevant substance(s) immobilized to other carriers such as plastic beads may be bound to the carbon-containing layer.

The immobilization of the biologically relevant substance (s) to the carbon-containing layer may be carried out by well-known methods through the above-described active group(s). For example, in cases where the active group is an amino group, the biologically relevant substance may be immobilized by converting the amino group to the corresponding anhydride with bromoacetic acid and carbodiimide; reacting the resultant with the amino group to bromoacetylate the surface; and then reacting the resultant with a sulfhydryl group in the biologically relevant substance such as a peptide. Alternatively, the biologically relevant substance can be immobilized through glutaraldehyde by reacting the amino group with the amino group in the biologically relevant molecule. In cases where the active group is an aldehyde group, the biologically relevant substance can be immobilized by the covalent bond with the amino group in the biomolecules desired to be immobilized. In cases where the active group is a carboxyl group, an ester is formed with N-hydroxysuccinimide, and the resulting ester can be bound to the amino group in the biologically relevant substance. In cases where the active group is a sulfhydryl group, the immobilization may be attained by selectively bromoacetylating the amino group in the biologically relevant molecule. Alternatively, the immobilization may be attained by binding the sulfhydryl group with the other sulfhydryl group through a disulfide. Further, the immobilization may be attained by selectively converting the amino group at the site to be subjected to the immobilization to maleimide, and reacting the resultant with the sulfhydryl group (for example, N-6 maleimide caproic acid is condensed with the amino group). In cases where the active group is an epoxy group, the biologically relevant substance may be immobilized similarly, by reaction of the epoxy group with biologically relevant substance having maleimides.

The present invention will now be described more concretely by way of Examples. However, the present invention is not restricted to the Examples.

EXAMPLE

Example 1

Preparation of Substrate for Biochip (Part 1)

1. Preparation of Carbon-Coated Aluminum Material

To 1 part by mass of a phenol resin, 4 parts by mass of a mixed solvent of toluene and methyl ethyl ketone (mixing ratio 1:1) is added, and the resultant was mixed to dissolve the phenol resin, and a coating solution having a solid content of 20% by mass was obtained. The coating solution was applied to both sides of an aluminum foil having a thickness of 50 μm and a purity of 99.3% by mass to form a resin layer, and the resin layer was dried at a temperature of 150° C. for 30 seconds. The thickness of the resin layer after drying was 1 to 3 μm on one side. Thereafter, the aluminum foil on both sides of which the resin layers were formed, was kept under methane gas atmosphere at a temperature of 550° C. for 10 hours to prepare a carbon-coated aluminum material in which an organic layer containing a carbon precursor, which organic layer is a carbon-containing layer, was formed.

Figure 3:
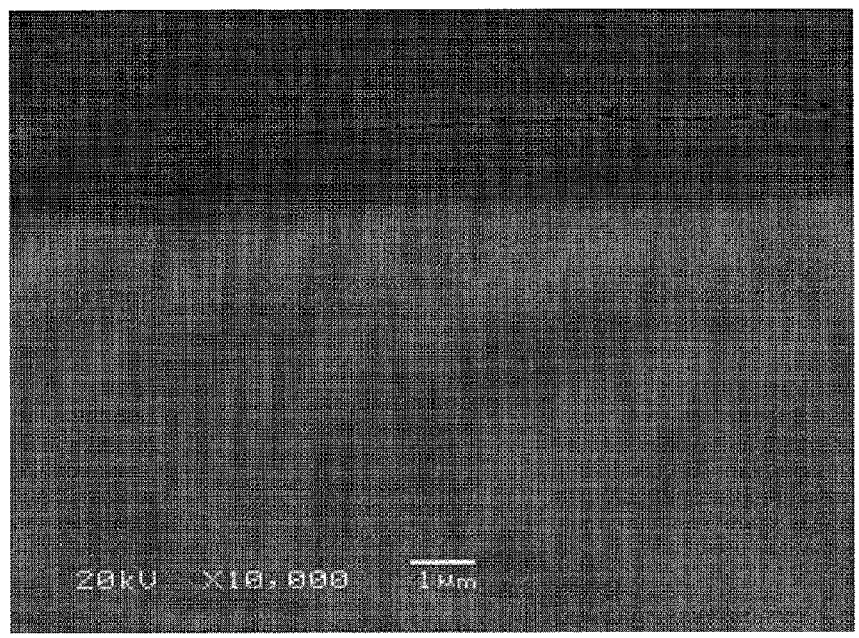
FIG. 3 is a SEM image showing the cross section of the carbon-coated aluminum material constituting the substrate for biochips, which substrate was produced in Example 1 of the present invention.
Figure 4:
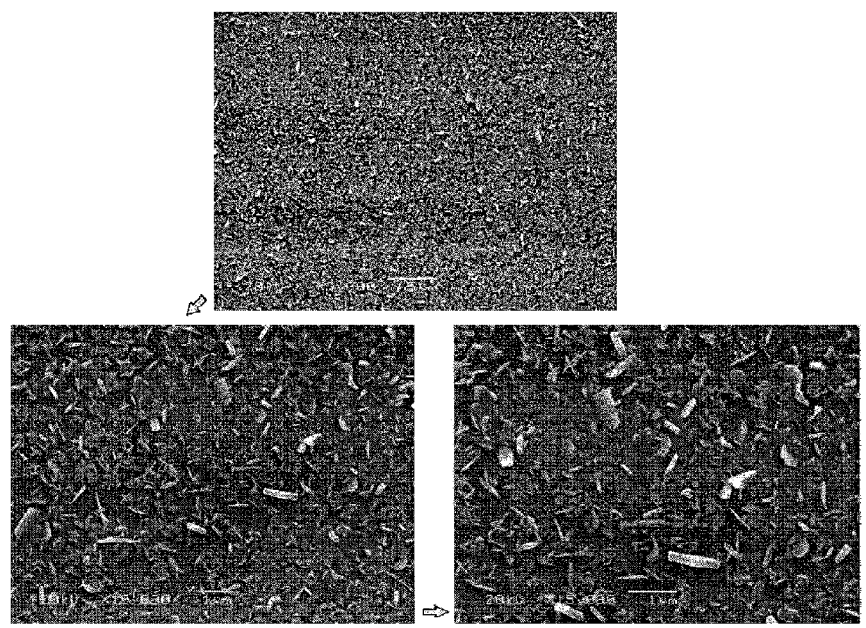
FIG. 4 is a SEM image showing the surface of the remaining interposing layer after dissolving and removing the aluminum material of the carbon-coated aluminum material constituting the substrate for biochips, which substrate was produced in Example 1 of the present invention.

The cross-section of the obtained carbon-coated aluminum material was observed to confirm that the organic layer was formed on the surface of the aluminum foil. The observation of the cross-section was carried out with a scanning election microscope (SEM). As an example, the cross-section of the carbon-coated aluminum material sample used in Example 1 was observed with a scanning election microscope (SEM), and the obtained photograph is shown in FIG. 3. The magnification of the photograph is ×10000. In order to observe the interposing layer of the carbon-coated aluminum material of Example 1, bromine-methanol mixture was used to dissolve aluminum portions, the surface of the remaining interposing layer 3 was directly observed with SEM, and the obtained photograph is shown in FIG. 4. That is, FIG. 4 is a photograph obtained by observing the back surface of the interposing layer exposed by removing the aluminum foil, in the direction from the interposing layer towards the carbon-containing layer. In FIG. 4, the magnification of the photograph is ×3000, ×10000 and ×15000 in order of arrows.

Figure 5:
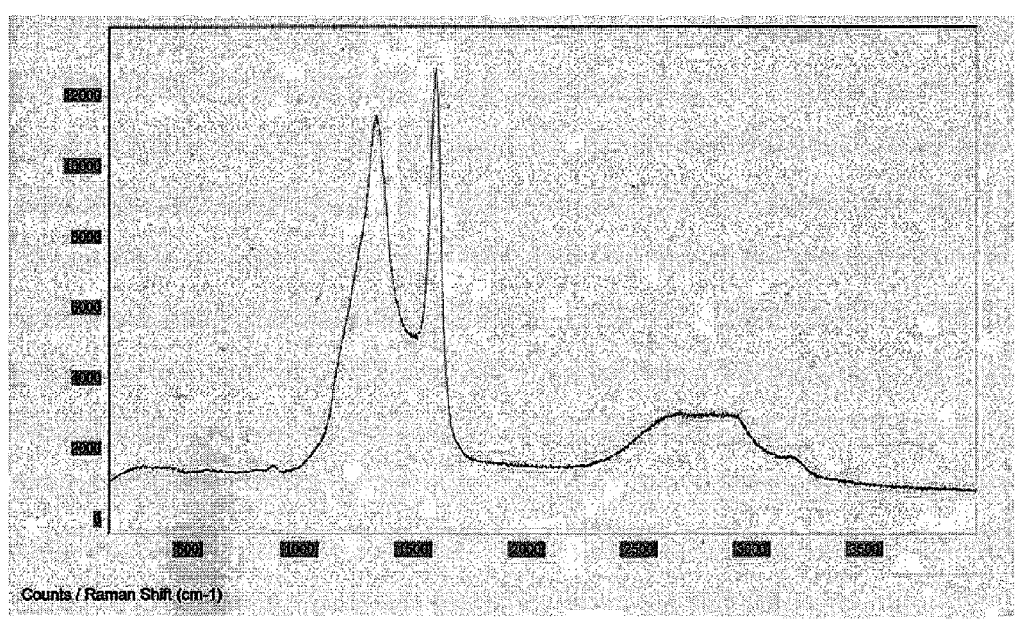
FIG. 5 shows the Raman spectrum detected by Raman spectroscopy of the organic layer of the carbon-coated aluminum material constituting the substrate for biochips of Example 1 of the present invention.

As show in FIG. 4, it can be well seen that in the carbon-coated aluminum material used in Example 1, many interposing layers are formed in the form of dispersed islands on the surface of the aluminum foil. The components contained in the organic layer in the carbon-coated aluminum material used in Example 1 were determined by Raman spectrum detected by Raman spectroscopy (measuring apparatus: microscopic Raman spectrometer Ramascope 1000 manufactured by RENISHAW). As a result, a peak of Raman scattering intensity, which corresponds to amorphous carbon, was detected at a Raman Shift of about 1350 cm$^{-1}$, and a peak of Raman scattering intensity, which corresponds to graphite, was further detected at a Raman Shift of about 1580 cm$^{-1}$ (FIG. 5). Since the peaks of Raman scattering intensity, which are thought to correspond to amorphous carbon component and graphite component, were detected in this Raman spectrum, it is assumed that carbon precursors are present in the organic layer in the carbon-coated aluminum material used in Example 1.

2. Lamination of Carbon-Coated Aluminum Material and Substrate Body

Next, the lamination of the obtained carbon-coated aluminum material and the substrate body was carried out. An aluminum plate (thickness 1 mm×width 25 mm×length 75 mm) was used as the substrate body, an ionomer resin film (thickness 50 μm×width 30 mm×length 80 mm) was put between the aluminum plate and the carbon-coated aluminum material (total thickness 54 μm×width 40 mm×length 90 mm) obtained in Example 1, and thermal adhesion of the aluminum plate and the carbon-coated aluminum material was carried out by pressing them with a hot plate type heat sealer (JIS HEAT SEALER produced by YASUDA SEIKI) at a hot plate temperature of 180° C. and a pressure of 3 kg/cm$^2$ for 5 seconds. The surplus portion from the size of the aluminum plate was cut to prepare a substrate for biochips of the present invention.

Example 2

Preparation of Carbon-Coated Aluminum Material (Part 2)

Carbon black particles having an average particle size of 300 nm in an amount of 2 parts by mass was mixed with 1 part by mass of polyvinyl chloride resin (in this case, the resin functions as a binder of the carbon black particles), and the resultant was dispersed in 12 parts by mass of a mixed solvent of toluene and methyl ethyl ketone (mixing ratio 1:1) to obtain a coating solution containing carbon black particles and having a solid content of 20% by mass. The coating solution was applied to both sides of an aluminum foil having a thickness of 50 μm and a purity of 99.3% by mass, and the applied coating was dried at a temperature of 150° C. for 30 seconds. The thickness of the carbon black particle-containing layer after drying was 1 μm for one side. Thereafter, the aluminum foil on both sides of which the carbon black particle-containing layers were formed, was kept under methane gas atmosphere at a temperature of 550° C. for 10 hours to form a carbon-containing layer. Thus, the carbon-coated aluminum material to be used in Example 2 was prepared.

Lamination of Carbon-Coated Aluminum Material and Substrate Body

Next, the lamination of the obtained carbon-coated aluminum material and the substrate body was carried out by the same method as in the lamination of the carbon-coated aluminum material and the aluminum plate as the substrate body in Example 1.

Example 6

Preparation of Carbon-Coated Aluminum Material (Part 3)

To 1 part by mass of a phenol resin, 4 parts by mass of a mixed solvent of toluene and methyl ethyl ketone (mixing ratio 1:1) was added, and the resulting solution was mixed to dissolve the phenol resin, and a coating solution having a solid content of 20% by mass was obtained. The coating solution was applied to both sides of an aluminum foil having a thickness of 50 μm and a purity of 99.3% by mass to form a resin layer, and the resin layer was dried at a temperature of 150° C. for 30 seconds. The thickness of the resin layer after drying was 1 to 2 μm for one side.

Further, 2 parts by mass of carbon black particles having an average particle size of 20 nm was mixed with 1 part by mass of a phenol resin, and the resultant was dispersed in 12 parts by mass of a mixed solvent of toluene and methyl ethyl ketone (mixing ratio 1:1) to obtain a coating solution containing carbon black particles and having a solid content of 20% by mass.

This coating solution was applied on the above-described resin layer, and the applied coating was dried at a temperature of 150° C. for 30 seconds. The thickness of the carbon black particle-containing layer after drying was 2 μm for one side.

Thereafter, the aluminum material on both sides of which the resin layer and the carbon black particle-containing layer were formed, was kept under methane gas atmosphere at a temperature of 550° C. for 10 hours to form a carbon-containing layer which is composed of a plurality of carbon-containing layers, in which the carbon-containing layer formed on the surface of the aluminum material among the plurality of carbon-containing layers (that is, the first layer which is other than the outermost layer) is composed of an organic layer containing a carbon precursor. Thus, the carbon-coated aluminum material to be used in Example 6 was prepared.

Lamination of Carbon-Coated Aluminum Material and Substrate Body

Next, the lamination of the obtained carbon-coated aluminum material and the substrate body was carried out by the same method as in the lamination of the carbon-coated aluminum material and the aluminum plate as the substrate body in Example 1.

Example 7

The carbon-coated aluminum material to be used in Example 2 was prepared in the same manner as in Example 2 except that the thickness of the carbon black particle-containing layer after drying was 2 μm for one side.
Lamination of Carbon-Coated Aluminum Material and Substrate Body Thereafter, the lamination of the obtained carbon-coated aluminum material and the substrate body was carried out by the same method as in the lamination of the carbon-coated aluminum material and the aluminum plate as the substrate body in Example 1.

Example 3

To different parts on each carbon-containing layer in the substrates for biochips obtained in Example 1 and Example 2 respectively, 0.2 μL each of water, dimethyl sulfoxide (DMSO) and dimethylformamide (DMF) was spotted to observe the spread of spots. For comparison, the substrate the entity of which was composed of amorphous carbon, and which was prepared by calcining the resin substrate for about one month, was also tested in the same way (Reference Example 1).

Figure 6:
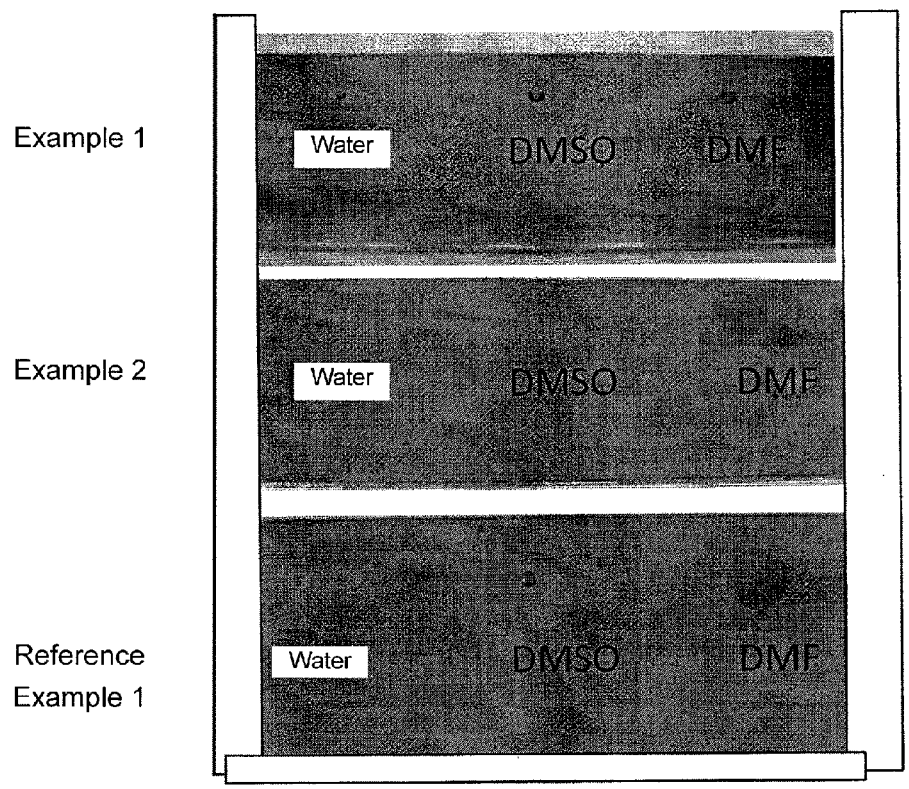
FIG. 6 is a photograph showing the spread of spots when adding water, DMSO and DMF dropwise on the substrate for biochips produced in Examples of the present invention and on the substrate of Reference Example the entire body of which substrate is composed of amorphous carbon.

The results are shown in FIG. 6. As shown in FIG. 6, as for the substrate obtained in Example 1, the spots did not spread at all in any cases where the above-described solvents were added dropwise. On the other hand, as for the amorphous carbon substrate of Reference Example 1, the spots did not spread in case of water and DMSO, whereas the spot spread in case of DMF. Also as for the substrate obtained in Example 2, although the spread of DMF is somewhat larger than that in Reference Example 1, almost the same results were obtained as in Reference Example 1. Since the spots did not spread in case of water and DMSO on the substrate obtained in Example 2 as on the substrate of Reference Example 1, the substrate obtained in Example 2 can also be used as the substrate for biochips by selecting the composition of the liquid to be used in the measurement. The substrate obtained in Example 1 is especially excellent as the substrate for biochips because the spot of DMF did not spread thereon, whereas the spot of DMF spread on the amorphous carbon substrate. It is presumed that the reason why the spot of DMF did not spread on the substrate obtained in Example 1 is because the carbon-containing layer is composed of an organic layer containing a carbon precursor to form small irregularities, and Lotus effect is generated due to the irregularities, thereby preventing diffusion of DMF to form oil droplets.

Example 4

Immobilization Example of DNA

Preparation of Substrate for Immobilizing DNA

The surface of the carbon-containing layer in the substrate for biochips obtained in Example 1 was coated with 1% by mass solution of polyacrylic acid having an average molecular weight of 5000 in ethanol to a thickness of 75 μm. The coated surface was dried in the air and then irradiated with UV light under reduced pressure at a degree of vacuum of 0.098 MPa with a low pressure mercury lamp for 4 minutes to immobilize polyacrylic acid on the substrate surface. Further, the unreacted polyacrylic acid was washed with pure water, and then the substrate was dried with a spin dryer to obtain a substrate for biochips for immobilizing DNA.
(Immobilization of Probe DNA)

To various parts on the substrate, 0.2 μL each of 10 μM probe DNA of 50-mer modified with amino groups at the terminals was spotted, and the resulting substrate was kept in an atmosphere at room temperature and a humidity of 100% RH for 8 hours. After washing the substrate under shaking with pure water for 5 minutes, the substrate was immersed in ethanol at 4° C. for 5 minutes and dried with a spin-dryer.
(DNA Hybridization)

100 μM Cy3-labeled DNA of 50-mer having a base sequence complementary to the above-described probe DNA was dissolved in a commercially available hybridization buffer solution to obtain 10 μM hybridization solution. The substrate was covered with a coverslip having a gap of 20 μm, and 30 μL of the hybridization solution was flown into the gap. The substrate was put into a lightproof bag laminated with aluminum, the humidity in the bag was set to 100% RH, and then the bag was left to stand in a dryer at 65° C. for 8 hours to carry out hybridization. After taking out the substrate from the bag, the substrate was washed for 5 minutes with a washing buffer solution which was prepared by adding sodium dodecyl benzene sulphonate (SDS) to 2×SSC buffer solution to a concentration of 0.1% by mass. Then, after washing the substrate with 0.2×SSC, 0.1% by mass of SDS buffer solution for 5 minutes, and with 0.2×SSC buffer solution for 5 minutes, the substrate was rinsed with pure water and dried with a spin-dryer.
(Fluorescence Measurement)

Fluorescence was measured for the whole surface of the substrate by employing exciting wavelength of 532 nm and measurement wavelength of 570 nm at a resolution of 10 μm with a fluorecent image scanner FLA-8000 commercially available from Fujifilm Corporation.

Figure 7:
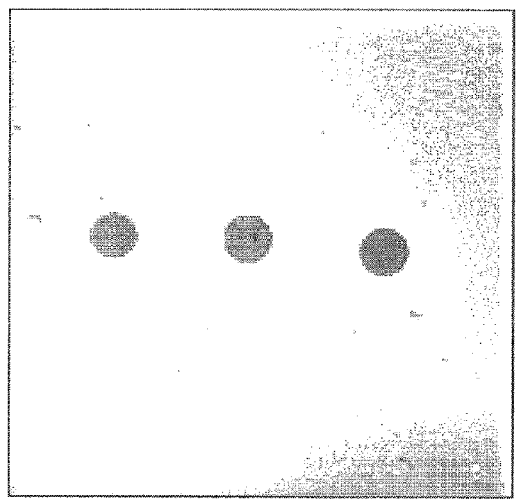
FIG. 7 is a photograph showing the measurement result of fluorescence, which result was obtained after adding the fluorescence-labeled DNA having a base sequence complementary to the DNA probe into the DNA probe-immobilized chip produced in Example below to hybridize DNA.

The measurement results are shown in FIG. 7. As is shown in FIG. 7, it can be seen that clear spots were observed. It can also be seen that the increase in background due to adsorption of unimmobilized DNA was not observed around the spots, and detection with high sensitivity can be attained without blocking functional groups on the surface.

Example 5

Immobilization Example of Protein

Preparation of Substrate for Immobilizing Protein

The surface of the carbon-containing layer in the substrate for biochips obtained in Example 1 was coated with 1% by mass solution of polyallylamine having an average molecular weight of 3000 in ethanol to a thickness of 75 μm. The coated surface was dried in the air and then irradiated with UV light under reduced pressure at a degree of vacuum of 0.098 MPa with a low pressure mercury lamp for 4 minutes to immobilize polyallylamine on the substrate surface. Further, the unreacted polyallylamine was washed with pure water, and then the substrate was dried with a spin dryer to obtain a substrate for biochips for immobilizing a protein.
(Immobilization of Protein)

A tetramethylrhodamine-labeled bovine serum albumin was dissolved in phosphate-buffered physiological saline (PBS) to a concentration of 0.1 mg/mL, and 10 mM of condensing agent 4-(4,6-dimethoxy-1,3,5-triazin-2-yl)-4-methylmorpholinium chloride (DMT-MM) was dissolved in the obtained phosphate-buffered physiological saline (PBS) to prepare a spot solution. To various parts on the substrate, 0.2 μL each of the spot solution was spotted, and the resulting substrate was kept in an atmosphere at room temperature and a humidity of 100% RH for 1 hour. The substrate was washed twice under shaking for 5 minutes with washing buffer obtained by dissolving Tween 20 (trade name) in PBS to a concentration of 0.1% by mass, and washed with PBS for 5 minutes. The substrate was rinsed with pure water, and then dried with a spin-dryer.

(Fluorescence Measurement)

Fluorescence was measured for the whole surface of the substrate by employing exciting wavelength of 532 nm and measurement wavelength of 570 nm at a resolution of 10 μm with a fluorecent image scanner FLA-8000 commercially available from Fujifilm Corporation.

Figure 8:
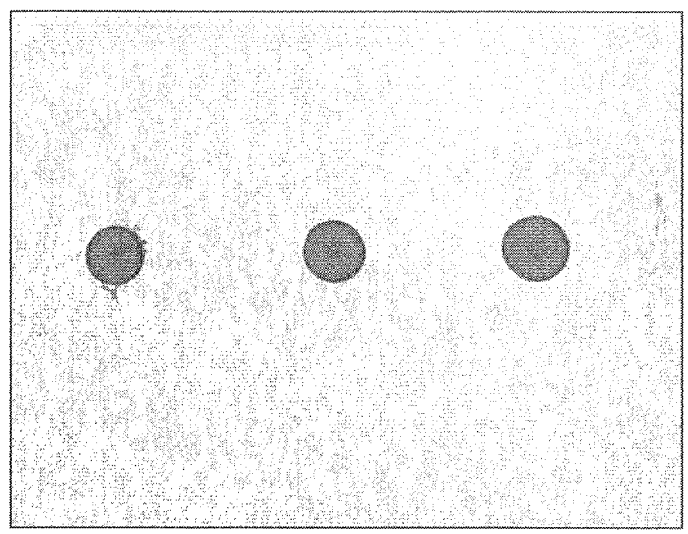
FIG. 8 is a photograph showing the measurement result of fluorescence, which result was obtained after adding the fluorescence-labeled bovine serum albumin to the biochip for immobilizing a protein, which biochip was produced in Example below, to immobilize the albumin.

The measurement results are shown in FIG. 8. As is shown in FIG. 8, it can be seen that clear spots were observed. It can also be seen that the increase in background due to adsorption of unimmobilized BSA is not observed around the spots, non-specific adsorption of a protein can be prevented by the substrate of the present invention, and therefore the detection of an immobilized protein with high sensitivity can be attained (Evaluation Method of Corrosion Resistance)

The edge of the substrate for biochips each obtained in Examples and Reference Examples respectively was subjected to masking with an epoxy adhesive to carry out anti-corrosion coating of the cross section of the substrate. The substrates were each immersed in 50 ml of phosphate-buffered physiological saline (chloride ion concentration: 2 mM, 150 mM) as a test fluid at room temperature for 4 hours. Then, after washing the substrate with pure water, the substrate was dried with a dryer at 60° C. for 30 minutes to check by visual observation whether the aluminum material on which a carbon-containing layer was formed, was corroded or not. When the aluminum material was corroded, the evaluation was "corroded"; when the aluminum material was corroded slightly, the evaluation was "corroded slightly"; and when the aluminum material was not corroded, the evaluation was "not corroded". The results are shown in Table 1.

The evaluation for the substrate of Example 6 was "not corroded" in any chloride ion concentration of 2 mM or 150 mM. It is presumed that this is because a plurality of carbon-containing layers are formed on the surface of the aluminum material in the substrate of Example 6, and the carbon-containing layer formed on the surface of the aluminum material among the plurality of carbon-containing layers (that is, the first layer other than the outermost layer) is composed of an organic layer containing a carbon precursor, which carbon-containing layer is compact and therefore functions as a barrier layer of the aluminum material, and penetration of physiological buffered saline into the surface of the aluminum material is prevented, thereby suppressing the corrosion of the aluminum material.

TABLE 1

|  | 150 mM | 2 mM |
| --- | --- | --- |
| Example 1 | corroded | not corroded |
| Example 2 | corroded | corroded |
| Example 6 | not corroded | not corroded |
| Example 7 | corroded | corroded slightly |
| Reference Example | not corroded | not corroded |

DESCRIPTION OF SYMBOLS

1 Aluminum material
2 Carbon-containing layer
3 Interposing layer
31 Fiber-like structure of interposing layer

The invention claimed is:

1. A substrate for biochips, said substrate comprising:
   (1) a carbon-coated aluminum material,
      wherein said carbon-coated aluminum material comprises:
      (a) an aluminum material,
      (b) a carbon-containing layer formed on at least one surface of said aluminum material, and
      (c) an interposing layer which is formed between said aluminum material and said carbon-containing layer,
         wherein said interposing layer contains aluminum element and carbon element; and
   (2) a substrate body,
      wherein said carbon-coated aluminum material is laminated on said substrate body.

2. The substrate for biochips, according to claim 1, wherein said carbon-containing layer is an organic layer containing a carbon precursor.

3. A substrate for biochips, said substrate comprising:
   a carbon-coated aluminum material,
      wherein said carbon-coated aluminum material comprises:
      (a) an aluminum material,
      (b) a carbon-containing layer formed on at least one surface of said aluminum material,
         wherein said carbon-containing layer is an organic layer containing a carbon precursor,
            wherein said carbon precursor contains at least carbon element and hydrogen element, and which has a peak(s) of Raman scattering intensity at a Raman Shift of about 1350 cm$^{-1}$ and/or about 1580 cm$^{-1}$ in Raman spectrum detected by Raman spectroscopy, and
      (c) an interposing layer which is formed between said aluminum material and said carbon-containing layer,
         wherein said interposing layer contains aluminum element and carbon element.

4. The substrate for biochips, according to claim 1, wherein said carbon-containing layer is composed of a plurality of carbon-containing layers, and the layer(s) other than the outermost layer among said plurality of carbon-containing layers is/are composed of an organic layer(s) containing a carbon precursor(s).

5. The substrate for biochips, according to claim 1, wherein said interposing layer is formed in the form of islands on the surface of said aluminum material.

6. The substrate for biochips, according to claim 1, which was subjected to an anticorrosion treatment of aluminum.

7. A substrate for biochips, said substrate comprising a carbon-coated aluminum material,
   wherein said carbon-coated aluminum material comprises:
   (a) an aluminum material,
   (b) a carbon-containing layer formed on at least one surface of said aluminum material, wherein
      said carbon-containing layer is an organic layer containing a carbon precursor, and
      an active group(s) for the binding with a biologically relevant substance(s) is/are bound to said carbon-containing layer, and
   (c) an interposing layer which is formed between said aluminum material and said carbon-containing layer, wherein said interposing layer contains aluminum element and carbon element.

8. A biochip in which one or more biologically relevant substances are bound on a substrate for biochips,
wherein said biochip substrate comprising a carbon-coated aluminum material,
wherein said carbon-coated aluminum material comprises:
(a) an aluminum material,
(b) a carbon-containing layer formed on at least one surface of said aluminum material, and
(c) an interposing layer which is formed between said aluminum material and said carbon-containing layer,
wherein said interposing layer contains aluminum element and carbon element.

9. A method for producing a substrate for biochips, said substrate comprising a carbon-coated aluminum material, wherein said method comprises the steps of:
a first step of providing an aluminum material;
a second step of placing said aluminum material in a space containing a hydrocarbon-containing substance; and
a third step of heating said aluminum material while being placed in the space containing the hydrocarbon-containing substance.

10. The method for producing a substrate for biochips, according to claim 9, which further comprises a forth step of laminating the obtained carbon-coated aluminum material on a substrate body after said third step.

11. The method for producing a substrate for biochips, according to claim 9 or 10, wherein said first step comprises a step of attaching a carbon-containing substance on the surface of the aluminum material.

12. The method for producing a substrate for biochips, according to claim 11, wherein the step of attaching a carbon-containing substance on the surface of said aluminum material is carried out a plurality of times.

13. A method for producing a biochip, said method comprising:
(1) a step of producing a substrate for biochips,
wherein said method for producing the substrate comprises the steps of:
(a) a first step of providing an aluminum material,
(b) a second step of placing said aluminum material in a space containing a hydrocarbon-containing substance, and
(c) a third step of heating said aluminum material while being placed in the space containing the hydrocarbon-containing substance; and
(2) a step of binding one or more biologically relevant substances on the obtained substrate for biochips.

* * * * *